United States Patent
Shu et al.

(10) Patent No.: US 11,246,848 B2
(45) Date of Patent: Feb. 15, 2022

(54) THREE-DIMENSIONAL CAGE-LIKE HYPERBRANCHED MONOMER, AND PREPARATION METHOD AND APPLICATION THEREOF

(71) Applicant: YANGTZE UNIVERSITY, Jingzhou (CN)

(72) Inventors: Wenming Shu, Jingzhou (CN); Weichu Yu, Jingzhou (CN); Jizhao Xing, Jingzhou (CN); Aibin Wu, Jingzhou (CN); Yaolu Li, Jingzhou (CN)

(73) Assignee: YANGTZE UNIVERSITY, Jingzhou (CN)

( * ) Notice: Subject to any disclaimer, the term of this patent is extended or adjusted under 35 U.S.C. 154(b) by 287 days.

(21) Appl. No.: 16/734,363

(22) Filed: Jan. 5, 2020

(65) Prior Publication Data

US 2021/0177791 A1    Jun. 17, 2021

(30) Foreign Application Priority Data

Dec. 13, 2019 (CN) .......................... 201911280961.1

(51) Int. Cl.
*A61K 31/197* (2006.01)
*C08G 83/00* (2006.01)
(Continued)

(52) U.S. Cl.
CPC .......... *A61K 31/197* (2013.01); *C08G 83/005* (2013.01); *C09K 8/035* (2013.01); *C09K 8/62* (2013.01)

(58) Field of Classification Search
None
See application file for complete search history.

(56) References Cited

U.S. PATENT DOCUMENTS

2013/0090269 A1* 4/2013 Luo ...................... C08F 220/56
507/226
2016/0115369 A1* 4/2016 Soriano, Jr. ............ C09K 8/524
507/90

(Continued)

*Primary Examiner* — John J Figueroa
(74) *Attorney, Agent, or Firm* — Hemisphere Law, PLLC; Zhigang Ma

(57) ABSTRACT

The invention discloses a three-dimensional cage-like hyperbranched monomer and preparation method and application thereof. The three-dimensional cage-like hyperbranched monomer has the structural formula I:

(Continued)

-continued

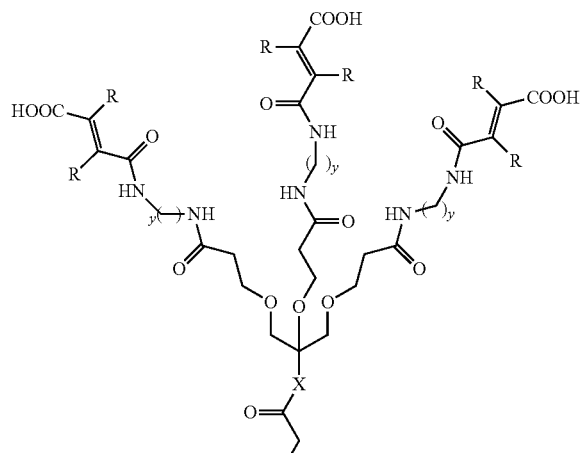

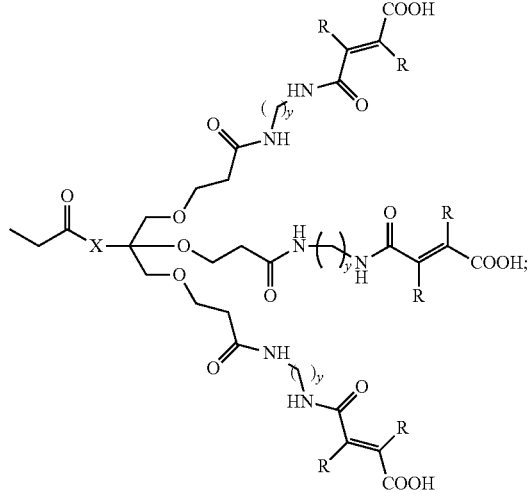

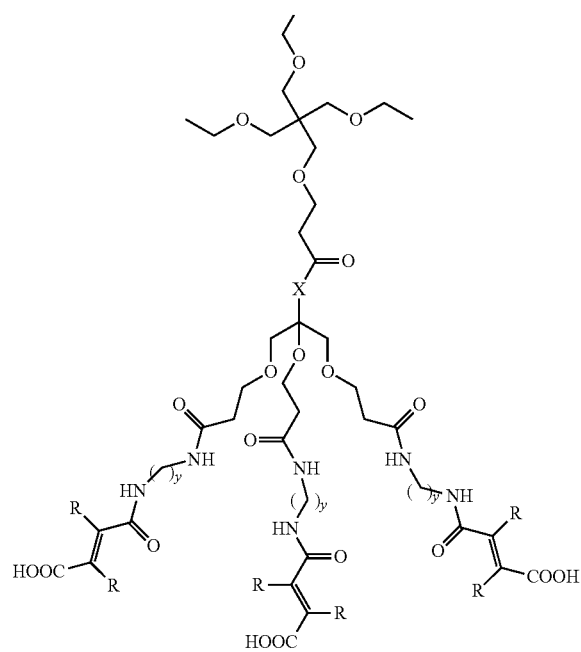

wherein in the structural formula I: X is any one of —O, —S, —NH; y is any integer from 2 to 8; R is —H or —$CH_3$. The beneficial effect of the technical scheme proposed in the present invention is: by introducing easily polymerizable olefin groups, the carboxyl group and amide group are combined in the three-dimensional cage-like hyperbranched monomer to make the water solubility good, and it can be copolymerized with many other monomers to obtain the three-dimensional cage-like hyperbranched polymer; when used as an additive for wellbore working fluids, due to the hyperbranched structure of the polymer, it has good salt and temperature resistance, and also has viscosity increasing, filtration loss, and flocculation properties; meanwhile, the synthesis method is simple and the cost is low.

9 Claims, 2 Drawing Sheets

(51) Int. Cl.
  *C09K 8/035* (2006.01)
  *C09K 8/62* (2006.01)

(56) References Cited

U.S. PATENT DOCUMENTS

2016/0333258 A1* 11/2016 Drake .................. E21B 37/00
2021/0108131 A1* 4/2021 Liu .................. C08F 220/56

* cited by examiner

THREE-DIMENSIONAL CAGE-LIKE HYPERBRANCHED MONOMER, AND PREPARATION METHOD AND APPLICATION THEREOF

FIELD OF THE DISCLOSURE

The disclosure relates to a three-dimensional cage-like hyperbranched monomer, and a preparation method and application thereof.

BACKGROUND

With the development of the petroleum industry, especially in recent years, our dependence on foreign oil and gas has become greater and greater. In order to ensure national energy security and vigorously improve the level of oil and gas exploration, higher requirements have been placed on oil and gas field extraction technologies. Especially the development of rock oil and gas fields is difficult, the working environment is complex, and the performance requirements of wellbore working fluids (including drilling fluids, completion fluids, and fracturing fluids) are higher. Due to the limitation of structure and group, the traditional wellbore working fluid can no longer meet the increasing performance requirements, which requires continuous design of new wellbore working fluid. In this process, molecular design has gradually gained attention, providing a more effective solution to these problems, which can not only improve the performance of the wellbore working fluid, but also meet the requirements of environmental protection.

At present, domestic and foreign wellbore working fluids can be divided into natural modified polymers, synthetic resins, and synthetic polymers according to their structure. Naturally modified polymer-type wellbore working fluids, mainly including modified starch, cellulose, lignin, humic acid, lignite, and tannin. They have a wide range of sources and low prices, but they generally have the weakness of low temperature and salt resistance. Synthetic resin type fluid loss reducer, such as the most commonly used sulfomethyl phenolic resin, is prepared by sulfonation reaction using phenolic resin as the precursor. Although it has good temperature resistance, salt resistance and filtration loss reduction properties, it is easy to cause environmental pollution during preparation and use. Therefore, the synthesis of new high temperature resistant, salt resistant and anti-calcium-magnesium fluid loss reducers is an issue we need to solve urgently. The key to solving the problem lies in the monomer with special structure and its synthesis method. Based on the concept of molecular design, a three-dimensional cage-like hyperbranched polymer with different groups and structures from traditional wellbore working fluids was designed to achieve the best results. Facts have proved that hyperbranched polymers can effectively improve the salt and temperature resistance of wellbore working fluids. However, the existing hyperbranched polymers have many synthetic steps, complicated synthetic processes, and insufficient performance. Therefore, the development of new three-dimensional cage-like hyperbranched monomers and new synthetic methods through organic synthesis reactions are very important to improve the performance of wellbore working fluids.

SUMMARY

The purpose of the present invention is to provide a three-dimensional cage-like hyperbranched monomer and preparation method and application thereof for solving the problems of unstable performance of a wellbore working fluid under high temperature and high salt conditions in the prior art.

The three-dimensional cage-like hyperbranched monomer has the structural formula I:

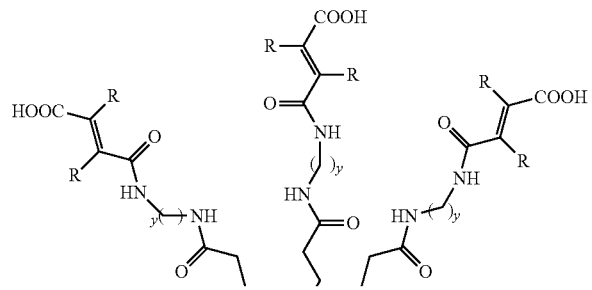

I

-continued

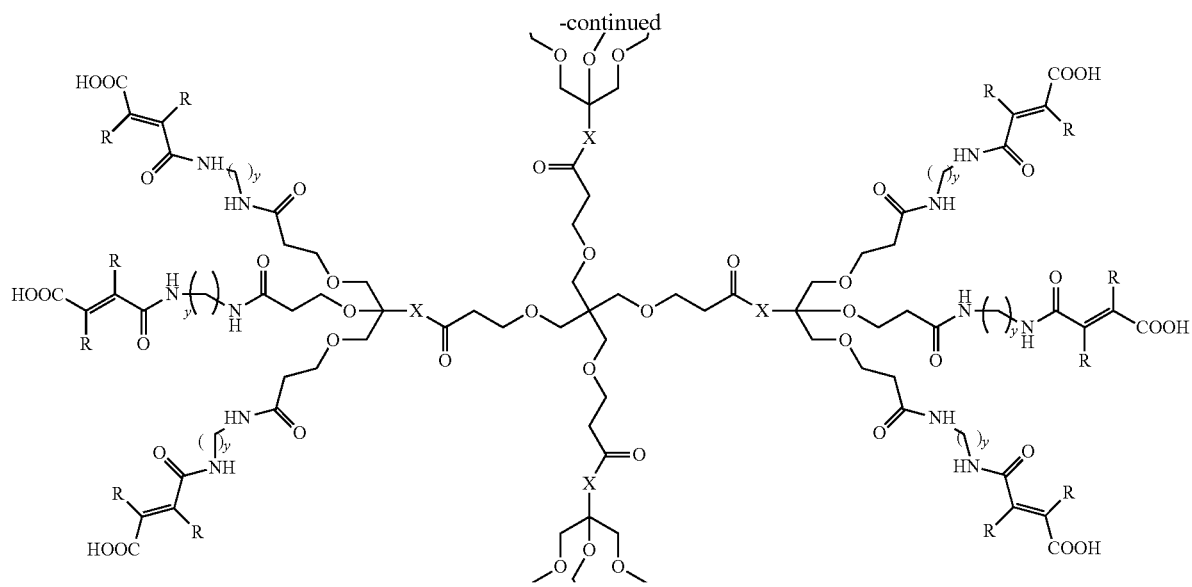

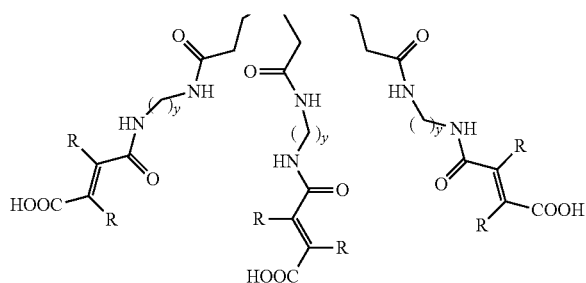

In the formula: X is any one of —O, —S, —NH; y is any integer from 2 to 8; R is —H or —CH$_3$.

The preparation method of the three-dimensional cage-like hyperbranched monomer, including the following steps:

(1) adding pentaerythritol and acrylonitrile to the reaction kettle in a molar ratio of 1:(4~4.5); under the condition of a solvent-free ice bath, slowly adding a 30% strength NaOH solution to the reaction kettle, keeping at room temperature and stirring with N$_2$ for 8~48 h; after the reaction is completed, a solvent is added, followed by extraction with an extractant; the extract is dried over anhydrous sodium sulfate, and the solvent is distilled off under reduced pressure to obtain an intermediate A, which has the structural formula II:

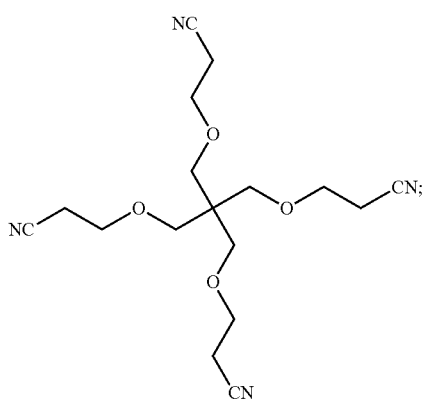

II (2) the intermediate A is added to concentrated hydrochloric acid and refluxed for 3~8 h to obtain intermediate B, whose structural formula is III:

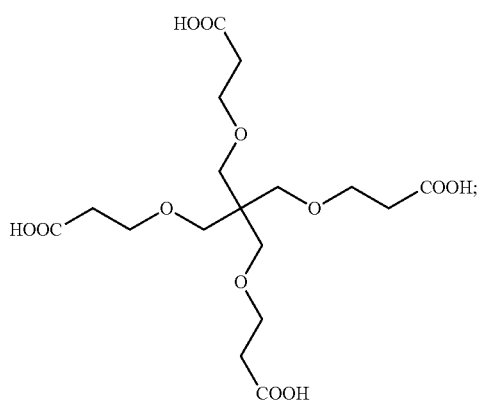

III (3) adding trimethylol-substituted methane, acrylonitrile, and 1,4-dioxane to the reaction kettle in a molar ratio of 1:(3~3.5): 20, and slowly adding a 40% strength NaOH solution to the reaction kettle; keeping at room temperature and stirring with $N_2$ for 8~48 h; after the reaction is completed, the solvent is added, followed by extraction with the extractant; the extract is dried over anhydrous sodium sulfate, and the solvent is distilled off under reduced pressure to obtain an intermediate C, which has the structural formula IV:

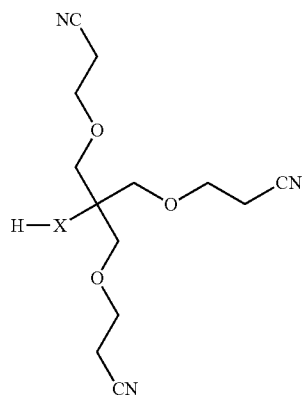

IV

X is any one of —O, —S, —NH;

(4) the intermediate C is added to a saturated HCl methanol solution, and refluxed for 3~8 h to obtain the intermediate D, whose structural formula is V:

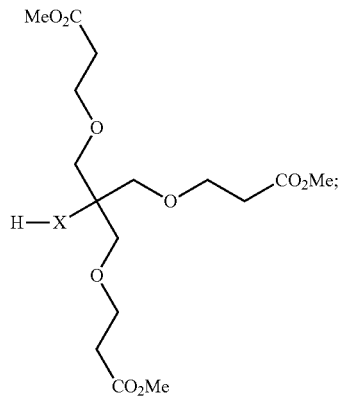

V (5) adding 1-(3-dimethylaminopropyl)-3-ethylcarbodiimide hydrochloride, 1-hydroxybenzotriazole, the intermediate B and the intermediate D to the reaction kettle containing the solvent in a molar ratio of 1:1:1:(4~5); keeping at room temperature and stirring with $N_2$ for 20~48 h; after the reaction is completed, it is extracted with the extractant, and then washed with saturated brine, dried over anhydrous sodium sulfate, and distilled under reduced pressure to obtain intermediate E, which has the structural formula VI:

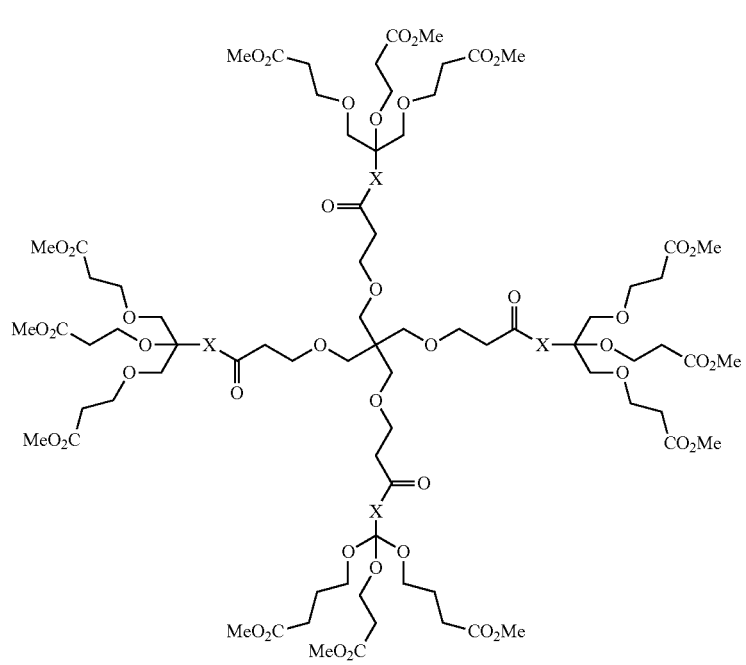
VI
X is any one of —O, —S, —NH;
(6) adding the intermediate E and the diamine in a molar ratio of 1:(12~20) to the reaction kettle containing the solvent, adding the diamine at 25~30° C. and stirring the reaction for 24~48 h; the solvent is then distilled off under reduced pressure to obtain intermediate F, which has the structural formula VII:
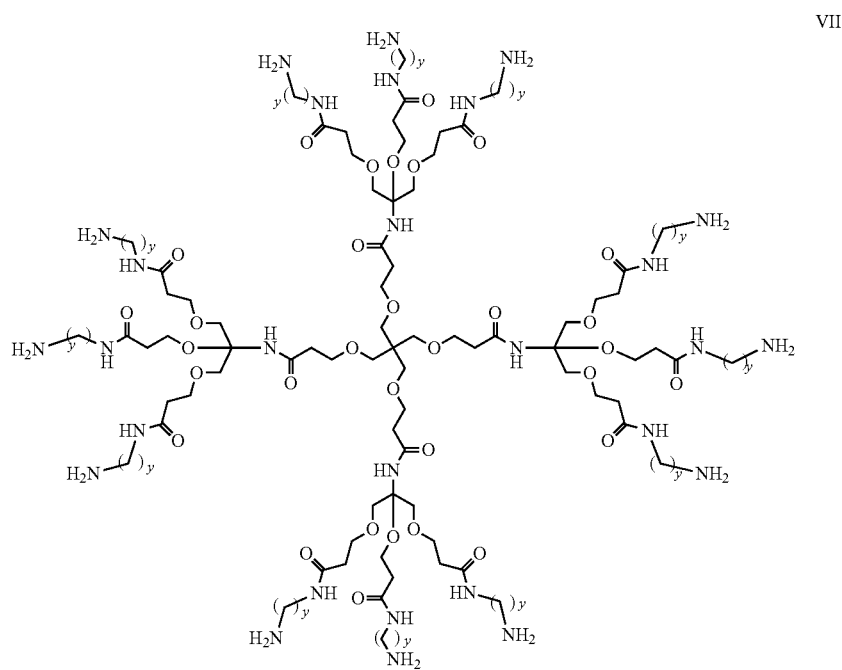
VII y is any integer from 2 to 8;

(7) under the condition of 25° C., the intermediate F, the acid binding agent and the dibasic anhydride are slowly added to the reaction kettle containing the solvent at a molar ratio of 1:12:(12~20), and then raising the temperature to 60~100° C. and reacting for 18~30 h; after the reaction is completed, the extractant is added for extraction, and the extract is washed with saturated brine, dried over anhydrous sodium sulfate, and the solvent is distilled off under reduced pressure to obtain the three-dimensional cage-like hyperbranched monomer previously.

The application of the three-dimensional cage-like hyperbranched monomer previously, wherein the three-dimensional cage-like hyperbranched monomer is used as an additive for a wellbore working fluid and a polymer emulsion; the wellbore working fluid includes drilling fluid, completion fluid, and fracturing fluid.

The beneficial effect of the technical scheme proposed in the present invention is: by introducing easily polymerizable olefin groups, the carboxyl group and amide group are combined in the three-dimensional cage-like hyperbranched monomer to make the water solubility good, and it can be copolymerized with many other monomers to obtain the three-dimensional cage-like hyperbranched polymer; when used as an additive for wellbore working fluids, due to the hyperbranched structure of the polymer, it has good salt and temperature resistance, and also has viscosity increasing, filtration loss, and flocculation properties; meanwhile, the synthesis method is simple and the cost is low.

BRIEF DESCRIPTION OF THE DRAWINGS

Accompanying drawings are for providing further understanding of embodiments of the disclosure. The drawings form a part of the disclosure and are for illustrating the principle of the embodiments of the disclosure along with the literal description. Apparently, the drawings in the description below are merely some embodiments of the disclosure, a person skilled in the art can obtain other drawings according to these drawings without creative efforts. In the figures.

DETAILED DESCRIPTION OF PREFERRED EMBODIMENTS

Figure 1:
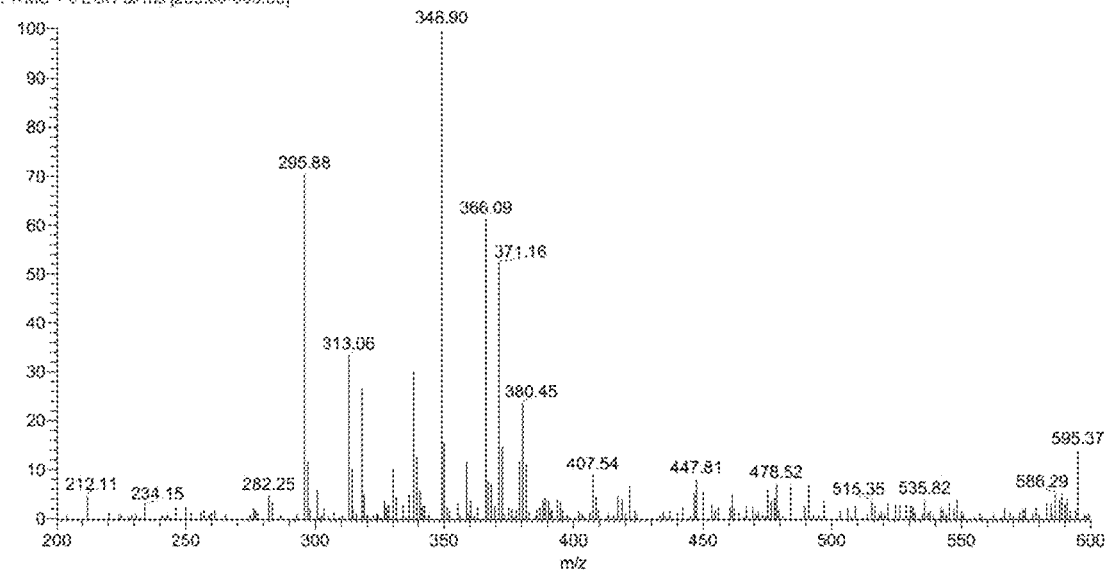
FIG. 1 is a mass spectrum of Intermediate A in Example 1 of the present invention.

For the first solution provided by the present invention, it is provided a three-dimensional cage-like hyperbranched monomer. The three-dimensional cage-like hyperbranched monomer has the structural formula I:

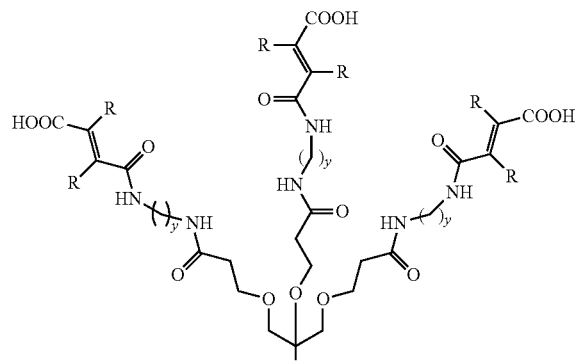

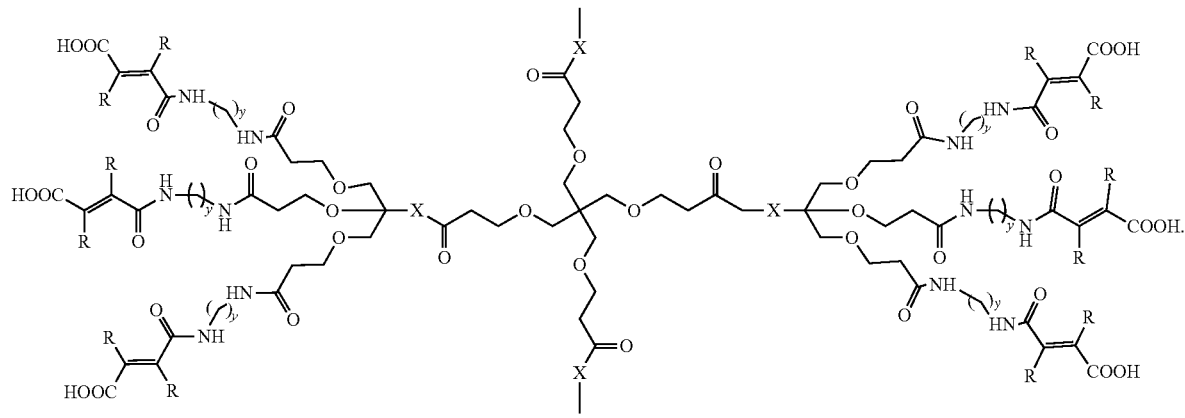

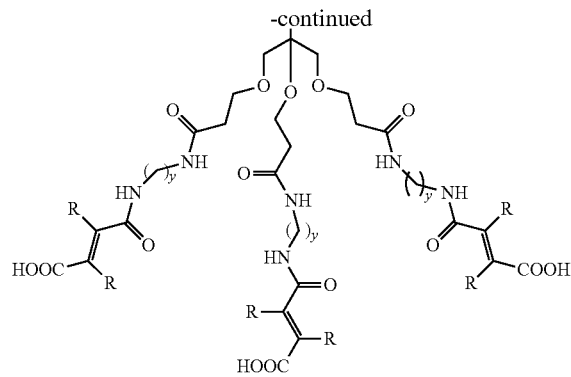

In the formula: X is any one of —O, —S, —NH; y is any integer from 2 to 8; R is —H or —CH$_3$.

For the second solution provided by the present invention, it is provided a preparation method of the three-dimensional cage-like hyperbranched monomer, including the following steps:

(1) adding pentaerythritol and acrylonitrile to the reaction kettle in a molar ratio of 1:(4~4.5); under the condition of a solvent-free ice bath, slowly adding a 30% strength NaOH solution to the reaction kettle, keeping at room temperature and stirring with N$_2$ for 8~48 h; after the reaction is completed, a solvent is added, followed by extraction with an extractant; the extract is dried over anhydrous sodium sulfate, and the solvent is distilled off under reduced pressure to obtain an intermediate A, which has the structural formula II:

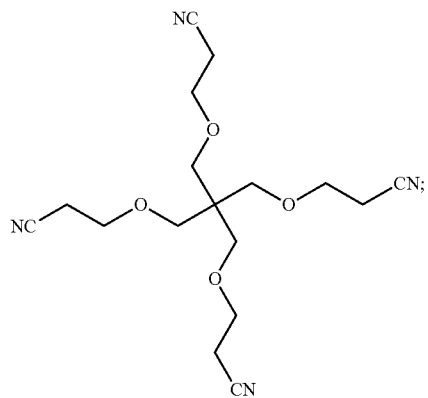

(2) the intermediate A is added to concentrated hydrochloric acid and refluxed for 3~8 h to obtain intermediate B, whose structural formula is III:

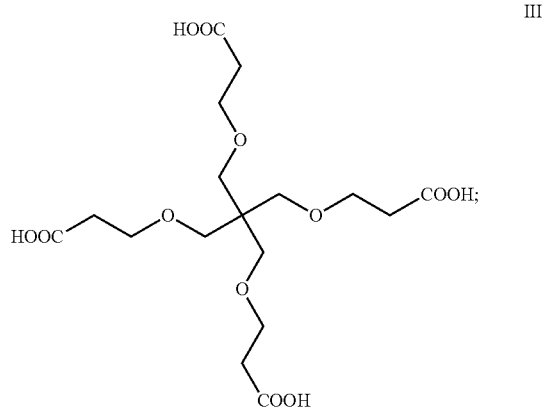 [SMILES: O=C(O)CCOCC(COCCC(=O)O)(COCCC(=O)O)COCCC(=O)O]

(3) adding trimethylol-substituted methane, acrylonitrile, and 1,4-dioxane to the reaction kettle in a molar ratio of 1:(3~3.5): 20, and slowly adding a 40% strength NaOH solution to the reaction kettle; keeping at room temperature and stirring with N$_2$ for 8~48 h; after the reaction is completed, the solvent is added, followed by extraction with the extractant; the extract is dried over anhydrous sodium sulfate, and the solvent is distilled off under reduced pressure to obtain an intermediate C, which has the structural formula IV:

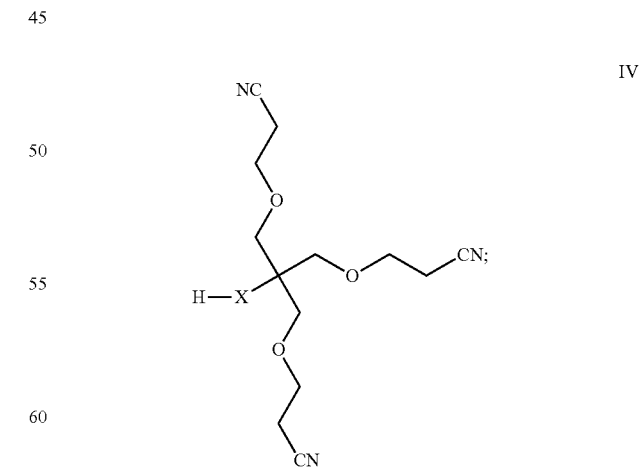

X is any one of —O, —S, —NH;

(4) the intermediate C is added to a saturated HCl methanol solution, and refluxed for 3~8 h to obtain the intermediate D, whose structural formula is V:

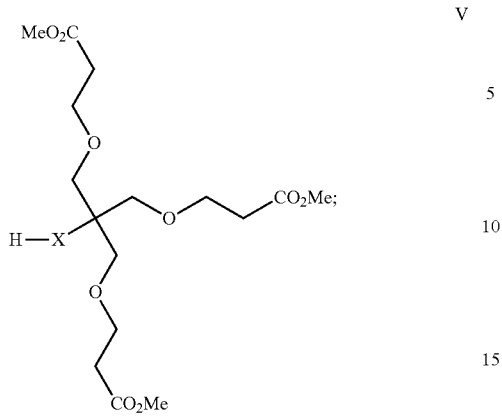

V (5) adding 1-(3-dimethylaminopropyl)-3-ethylcarbodiimide hydrochloride, 1-hydroxybenzotriazole, the intermediate B and the intermediate D to the reaction kettle containing the solvent in a molar ratio of 1:1:1:(4~5); keeping at room temperature and stirring with $N_2$ for 20~48 h; after the reaction is completed, it is extracted with the extractant, and then washed with saturated brine, dried over anhydrous sodium sulfate, and distilled under reduced pressure to obtain intermediate E, which has the structural formula VI:

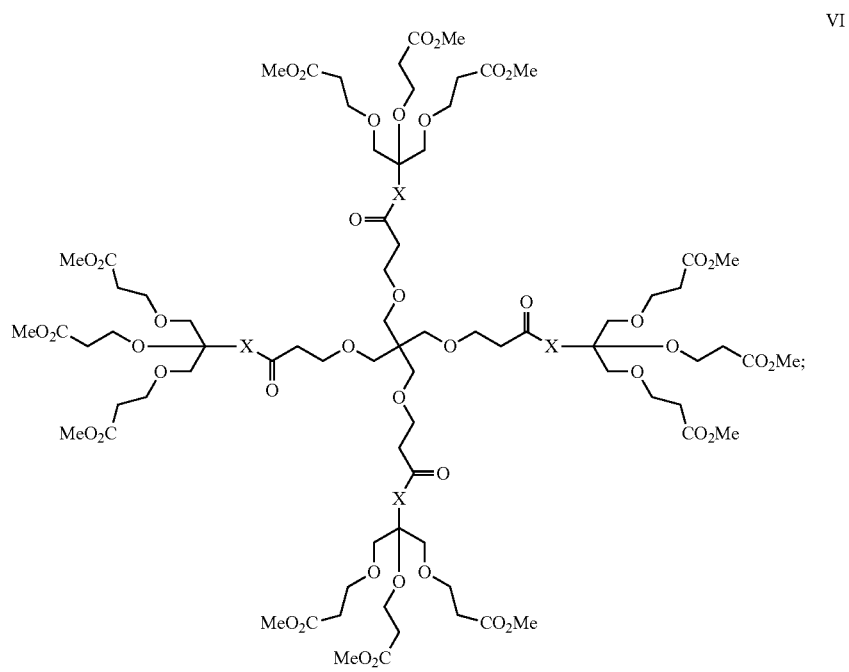

VI

X is any one of —O, —S, —NH;

(6) adding the intermediate E and the diamine in a molar ratio of 1:(12~20) to the reaction kettle containing the solvent, adding the diamine at 25~30° C. and stirring the reaction for 24~48 h; the solvent is then distilled off under reduced pressure to obtain intermediate F, which has the structural formula VII:

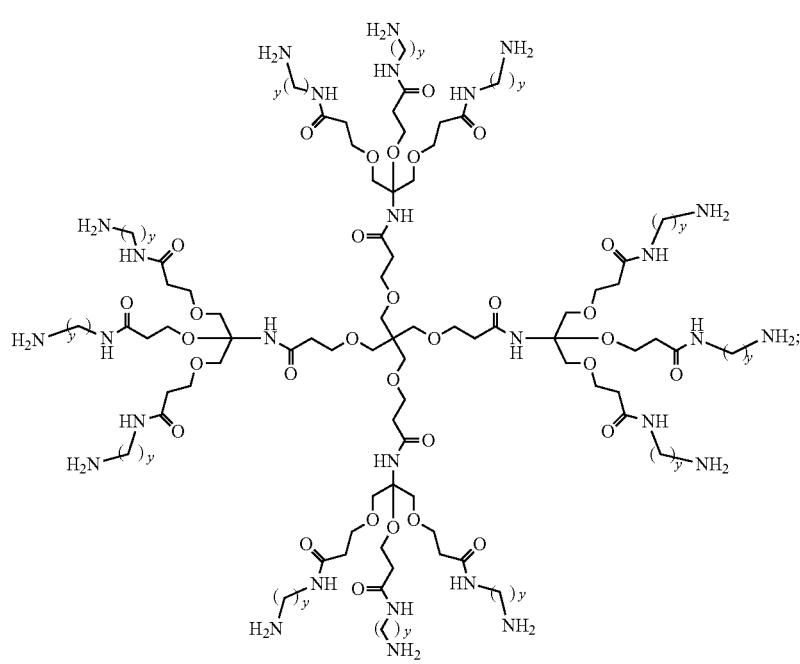

VII y is any integer from 2 to 8;

(7) under the condition of 25° C., the intermediate F, the acid binding agent and the dibasic anhydride are slowly added to the reaction kettle containing the solvent at a molar ratio of 1:12:(12~20), and then raising the temperature to 60~100° C. and reacting for 18~30 h; after the reaction is completed, the extractant is added for extraction, and the extract is washed with saturated brine, dried over anhydrous sodium sulfate, and the solvent is distilled off under reduced pressure to obtain the three-dimensional cage-like hyperbranched monomer in the first solution.

In this embodiment, the trimethylol-substituted methane is one of tris(hydroxymethyl)methane, tris(hydroxymethyl)mercaptomethane and tris(hydroxymethyl)aminomethane; the diamine is one of ethylenediamine, propylenediamine, butylenediamine, pentanediamine, hexamethylenediamine, diaminoheptane and octanediamine; the dibasic acid anhydride is maleic anhydride or 2,3-dimethyl maleic anhydride; the solvent is one or a mixture of dioxane, dichloromethane, dichloroethane, chloroform, methanol, water, methanol, ethanol, isopropanol, tert-butanol, diethyl ether, isopropyl ether, petroleum ether, acetone, tetrahydrofuran, N,N-dimethylformamide, N,N-dimethylacetamide, dimethyl sulfoxide and white oil; the acid binding agent is one or a mixture of triethylamine, tri-n-propylamine, tri-n-butylamine, N,N,N',N'-tetramethylethylenediamine or triethylenediamine; the extractant is one or a mixture of ethyl acetate, dichloromethane, chloroform, and dichloroethane.

For the third solution provided by the present invention, it is provided an application of the three-dimensional cage-like hyperbranched monomer. The three-dimensional cage-like hyperbranched monomer is used as an additive for a wellbore working fluid and a polymer emulsion; the wellbore working fluid includes drilling fluid, completion fluid, and fracturing fluid.

In this embodiment, When the three-dimensional cage-like hyperbranched monomer is practically used, the three-dimensional cage-like hyperbranched monomer can copolymerize with other monomers, thereby exerting the effects of resistance to salt, temperature, viscosity, and filtration loss. The other monomers here may be non-ionic monomers, cationic monomers, anionic monomers or zwitterionic monomers. Among them, the cationic monomer includes one or more of dimethyl diallyl ammonium chloride, diethyl diallyl ammonium chloride, dimethyl aminoethyl methacrylate, dimethyl aminoethyl acrylate, methacryloyloxyethyl trimethyl ammonium chloride, 3-acrylamidopropyl trimethylammonium chloride, 3-acryloyloxypropyl trimethylammonium chloride, 3-acrylamidopropyl dimethyl propane ammonium sulfonate, 3-acrylamide 2-hydroxydimethylammonium chloride, 3-acryloyloxyethyldiethylpropanesulfonate, 3-acryloyloxyethyl dimethyl propane ammonium sulfonate, 3-acrylamidopropyl dimethylammonium chloride or 3-acryloyloxyethyl diisopropyl propane ammonium sulfonate; the anionic monomer includes one or more of 2-acrylamido-2-methyl propane sulfonic acid, 2-acrylamido dodecyl sulfonic acid, 2-acrylamido tetradecanyl sulfonic acid, 2-acrylamido hexadecyl sulfonic acid, Acrylic oxy butyl sulfonic acid, 2-acryloyloxy-2-methyl propane sulfonic acid, acrylic acid, methacrylic acid, maleic anhydride or itaconic acid; zwitterionic monomer includes one or more of acrylamide, acrylonitrile, methyl acrylate, ethyl acrylate, N-methyl pyrrolidone, N,N-dimethyl acrylamide, N,N-diethyl acrylamide, isobutylene acrylamide, vinyl formamide, vinyl acetamide, styrene, hydroxyethyl acrylate, hydroxypropyl acrylate, hydroxyethyl methacrylate, hydroxypropyl methacrylate.

For the copolymerization reaction conditions when the three-dimensional cage-like hyperbranched monomer is used, the reaction temperature is preferably 10~80° C., the reaction time is 0.5~10 h, and the pH is 5~12. At the same time, an appropriate initiator is needed to activate the copolymerization reaction when the copolymerization reaction is performed. In this embodiment, the amount of the initiator is preferably 0.01~0.10% of the total mass of the three-dimensional cage-like hyperbranched monomer. The initiator used in the copolymerization reaction is one or a mixture of a radical initiator or a redox initiator. The radical initiator includes one or more of 2,2'-azobisisobutyronitrile, 2,2'-azodi(2-methylbutyronitrile), 2,2'-azobisisoheptonitrile, 2,2'-azobis[2-(2-imidazolin-2-yl)propane], 2,2'-azobis(2-methylpropionamidine)dihydrochloride 1,2-bis(2-(4,5-dihydro-1H-imidazol-2-yl)propan-2-yl)diazene dihydrochloride, dimethyl 2,2'-azobis(2-methylpropionate), 1,1'-azobiscarbamide, 1[(1-cyano-1-methylethyl)azo]formamide, 1,1'-azobis(cyclohexane-1-carbonitrile), 4,4'-azobis(4-cyanovaleric acid); the redox initiator includes one or more of potassium persulfate-sodium sulfite, potassium persulfate-potassium sulfite, potassium persulfate-ammonium sulfite, sodium persulfate-sodium sulfite, sodium persulfate-potassium sulfite, sodium persulfate-ammonium sulfite, Ammonium persulfate-sodium sulfite, ammonium persulfate-potassium sulfite, ammonium persulfate-ammonium sulfite, potassium persulfate-thiourea, sodium persulfate-thiourea or ammonium persulfate.

The three-dimensional cage-like hyperbranched monomer, its preparation method and application will be further described in combination with specific embodiment.

Example 1

(1) Adding pentaerythritol and acrylonitrile to the reaction kettle in a molar ratio of 1:4.2; under the condition of a solvent-free ice bath, slowly adding a 30% strength NaOH solution to the reaction kettle, keeping at room temperature and stirring with $N_2$ for 8~48 h; after the reaction is completed, water is added, followed by extraction with ethyl acetate; the extract is dried over anhydrous sodium sulfate, and the solvent is distilled off under reduced pressure to obtain the intermediate A.

(2) The intermediate A is added to concentrated hydrochloric acid and refluxed for 5 h to obtain intermediate B.

(3) Adding tris(hydroxymethyl)aminomethane, acrylonitrile, and 1,4-dioxane to the reaction kettle in a molar ratio of 1:3.1:20, the mount of 1,4-dioxane is 10 mL, and slowly adding a 40% strength NaOH solution to the reaction kettle; keeping at room temperature and stirring with $N_2$ for 36 h; after the reaction is completed, the solvent is added, followed by extraction with ethyl acetate; the extract is dried over anhydrous sodium sulfate, and the solvent is distilled off under reduced pressure to obtain an intermediate C.

(4) The intermediate C is added to a saturated HCl methanol solution, and refluxed for 8 h to obtain the intermediate D.

(5) Adding 1-(3-dimethylaminopropyl)-3-ethylcarbodiimide hydrochloride, 1-hydroxybenzotriazole, the intermediate B and the intermediate D to the reaction kettle containing dichloromethane solvent in a molar ratio of 1:1:1:4.2; keeping at room temperature and stirring with $N_2$ for 30 h; after the reaction is completed, it is extracted with dichloromethane, and then washed with saturated brine, dried over anhydrous sodium sulfate, and distilled under reduced pressure to obtain intermediate E.

(6) Adding the intermediate E and ethylenediamine in a molar ratio of 1:12 to the reaction kettle containing the solvent, adding ethylenediamine at 25~30° C. and stirring the reaction for 48 h; the solvent is then distilled off under reduced pressure to obtain intermediate F.

(7) Under the condition of 25° C., the intermediate F, triethylamine and maleic anhydride are slowly added to the reaction kettle containing the solvent at a molar ratio of 1:12:15, and then raising the temperature to 80° C. and reacting for 24 h; after the reaction is completed, ethyl acetate is added for extraction, and the extract is washed with saturated brine, dried over anhydrous sodium sulfate, and the solvent is distilled off under reduced pressure to obtain the three-dimensional cage-like hyperbranched monomer sample 1.

Example 2

(1) Adding pentaerythritol and acrylonitrile to the reaction kettle in a molar ratio of 1:4.2; under the condition of a solvent-free ice bath, slowly adding a 30% strength NaOH solution to the reaction kettle, keeping at room temperature and stirring with $N_2$ for 8~48 h; after the reaction is completed, water is added, followed by extraction with ethyl acetate; the extract is dried over anhydrous sodium sulfate, and the solvent is distilled off under reduced pressure to obtain the intermediate A.

(2) The intermediate A is added to concentrated hydrochloric acid and refluxed for 5 h to obtain intermediate B.

(3) Adding tris(hydroxymethyl)methane, acrylonitrile, and 1,4-dioxane to the reaction kettle in a molar ratio of 1:3.1:20, the mount of 1,4-dioxane is 10 mL, and slowly adding a 40% strength NaOH solution to the reaction kettle; keeping at room temperature and stirring with $N_2$ for 36 h; after the reaction is completed, the solvent is added, followed by extraction with ethyl acetate; the extract is dried over anhydrous sodium sulfate, and the solvent is distilled off under reduced pressure to obtain an intermediate C.

(4) The intermediate C is added to a saturated HCl methanol solution, and refluxed for 8 h to obtain the intermediate D.

(5) Adding 1-(3-dimethylaminopropyl)-3-ethylcarbodiimide hydrochloride, 1-hydroxybenzotriazole, the intermediate B and the intermediate D to the reaction kettle containing dichloromethane solvent in a molar ratio of 1:1:1:4.2; keeping at room temperature and stirring with $N_2$ for 30 h; after the reaction is completed, it is extracted with dichloromethane, and then washed with saturated brine, dried over anhydrous sodium sulfate, and distilled under reduced pressure to obtain intermediate E.

(6) Adding the intermediate E and ethylenediamine in a molar ratio of 1:12 to the reaction kettle containing the solvent, adding ethylenediamine at 25~30° C. and stirring the reaction for 48 h; the solvent is then distilled off under reduced pressure to obtain intermediate F.

(7) Under the condition of 25° C., the intermediate F, triethylamine and maleic anhydride are slowly added to the reaction kettle containing the solvent at a molar ratio of 1:12:15, and then raising the temperature to 80° C. and reacting for 24 h; after the reaction is completed, ethyl acetate is added for extraction, and the extract is washed with saturated brine, dried over anhydrous sodium sulfate, and the solvent is distilled off under reduced pressure to obtain the three-dimensional cage-like hyperbranched monomer sample 2.

Example 3

(1) Adding pentaerythritol and acrylonitrile to the reaction kettle in a molar ratio of 1:4.2; under the condition of a solvent-free ice bath, slowly adding a 30% strength NaOH solution to the reaction kettle, keeping at room temperature and stirring with $N_2$ for 8~48 h; after the reaction is completed, water is added, followed by extraction with ethyl acetate; the extract is dried over anhydrous sodium sulfate, and the solvent is distilled off under reduced pressure to obtain the intermediate A.

(2) The intermediate A is added to concentrated hydrochloric acid and refluxed for 5 h to obtain intermediate B.

(3) Adding tris(hydroxymethyl)mercaptomethane, acrylonitrile, and 1,4-dioxane to the reaction kettle in a molar ratio of 1:3.1:20, the mount of 1,4-dioxane is 10 mL, and slowly adding a 40% strength NaOH solution to the reaction kettle; keeping at room temperature and stirring with $N_2$ for 36 h; after the reaction is completed, the solvent is added, followed by extraction with ethyl acetate; the extract is dried over anhydrous sodium sulfate, and the solvent is distilled off under reduced pressure to obtain an intermediate C.

(4) The intermediate C is added to a saturated HCl methanol solution, and refluxed for 8 h to obtain the intermediate D.

(5) Adding 1-(3-dimethylaminopropyl)-3-ethylcarbodiimide hydrochloride, 1-hydroxybenzotriazole, the intermediate B and the intermediate D to the reaction kettle containing dichloromethane solvent in a molar ratio of 1:1:1:4.2; keeping at room temperature and stirring with $N_2$ for 30 h; after the reaction is completed, it is extracted with dichloromethane, and then washed with saturated brine, dried over anhydrous sodium sulfate, and distilled under reduced pressure to obtain intermediate E.

(6) Adding the intermediate E and ethylenediamine in a molar ratio of 1:12 to the reaction kettle containing the solvent, adding ethylenediamine at 25~30° C. and stirring the reaction for 48 h; the solvent is then distilled off under reduced pressure to obtain intermediate F.

(7) Under the condition of 25° C., the intermediate F, triethylamine and maleic anhydride are slowly added to the reaction kettle containing the solvent at a molar ratio of 1:12:15, and then raising the temperature to 80° C. and reacting for 24 h; after the reaction is completed, ethyl acetate is added for extraction, and the extract is washed with saturated brine, dried over anhydrous sodium sulfate, and the solvent is distilled off under reduced pressure to obtain the three-dimensional cage-like hyperbranched monomer sample 3.

Example 4

(1) Adding pentaerythritol and acrylonitrile to the reaction kettle in a molar ratio of 1:4.2; under the condition of a solvent-free ice bath, slowly adding a 30% strength NaOH solution to the reaction kettle, keeping at room temperature and stirring with $N_2$ for 8~48 h; after the reaction is completed, water is added, followed by extraction with ethyl acetate; the extract is dried over anhydrous sodium sulfate, and the solvent is distilled off under reduced pressure to obtain the intermediate A.

(2) The intermediate A is added to concentrated hydrochloric acid and refluxed for 5 h to obtain intermediate B.

(3) Adding tris(hydroxymethyl)aminomethane, acrylonitrile, and 1,4-dioxane to the reaction kettle in a molar ratio of 1:3.1:20, the mount of 1,4-dioxane is 10 mL, and slowly adding a 40% strength NaOH solution to the reaction kettle; keeping at room temperature and stirring with $N_2$ for 36 h; after the reaction is completed, the solvent is added, followed by extraction with ethyl acetate; the extract is dried over anhydrous sodium sulfate, and the solvent is distilled off under reduced pressure to obtain an intermediate C.

(4) The intermediate C is added to a saturated HCl methanol solution, and refluxed for 8 h to obtain the intermediate D.

(5) Adding 1-(3-dimethylaminopropyl)-3-ethylcarbodiimide hydrochloride, 1-hydroxybenzotriazole, the intermediate B and the intermediate D to the reaction kettle containing dichloromethane solvent in a molar ratio of 1:1:1:4.3; keeping at room temperature and stirring with $N_2$ for 30 h; after the reaction is completed, it is extracted with dichloromethane, and then washed with saturated brine, dried over anhydrous sodium sulfate, and distilled under reduced pressure to obtain intermediate E.

(6) Adding the intermediate E and propane-diamine in a molar ratio of 1:12 to the reaction kettle containing the solvent, adding propane-diamine at 25~30° C. and stirring the reaction for 48 h; the solvent is then distilled off under reduced pressure to obtain intermediate F.

(7) Under the condition of 25° C., the intermediate F, triethylamine and maleic anhydride are slowly added to the reaction kettle containing the solvent at a molar ratio of 1:12:15, and then raising the temperature to 80° C. and reacting for 24 h; after the reaction is completed, ethyl acetate is added for extraction, and the extract is washed with saturated brine, dried over anhydrous sodium sulfate, and the solvent is distilled off under reduced pressure to obtain the three-dimensional cage-like hyperbranched monomer sample 4.

Example 5

(1) Adding pentaerythritol and acrylonitrile to the reaction kettle in a molar ratio of 1:4.2; under the condition of a solvent-free ice bath, slowly adding a 30% strength NaOH solution to the reaction kettle, keeping at room temperature and stirring with $N_2$ for 8~48 h; after the reaction is completed, water is added, followed by extraction with ethyl acetate; the extract is dried over anhydrous sodium sulfate, and the solvent is distilled off under reduced pressure to obtain the intermediate A.

(2) The intermediate A is added to concentrated hydrochloric acid and refluxed for 5 h to obtain intermediate B.

(3) Adding tris(hydroxymethyl)aminomethane, acrylonitrile, and 1,4-dioxane to the reaction kettle in a molar ratio of 1:3.1:20, the mount of 1,4-dioxane is 10 mL, and slowly adding a 40% strength NaOH solution to the reaction kettle; keeping at room temperature and stirring with $N_2$ for 36 h; after the reaction is completed, the solvent is added, followed by extraction with ethyl acetate; the extract is dried over anhydrous sodium sulfate, and the solvent is distilled off under reduced pressure to obtain an intermediate C.

(4) The intermediate C is added to a saturated HCl methanol solution, and refluxed for 8 h to obtain the intermediate D.

(5) Adding 1-(3-dimethylaminopropyl)-3-ethylcarbodiimide hydrochloride, 1-hydroxybenzotriazole, the intermediate B and the intermediate D to the reaction kettle containing dichloromethane solvent in a molar ratio of 1:1:1:4.3; keeping at room temperature and stirring with $N_2$ for 30 h; after the reaction is completed, it is extracted with dichloromethane, and then washed with saturated brine, dried over anhydrous sodium sulfate, and distilled under reduced pressure to obtain intermediate E.

(6) Adding the intermediate E and ethylenediamine in a molar ratio of 1:12 to the reaction kettle containing the solvent, adding ethylenediamine at 25~30° C. and stirring the reaction for 48 h; the solvent is then distilled off under reduced pressure to obtain intermediate F.

(7) Under the condition of 25° C., the intermediate F and maleic anhydride are slowly added to the reaction kettle containing the solvent at a molar ratio of 1:13, and then raising the temperature to 80° C. and reacting for 24 h; after the reaction is completed, ethyl acetate is added for extraction, and the extract is washed with saturated brine, dried over anhydrous sodium sulfate, and the solvent is distilled off under reduced pressure to obtain the three-dimensional cage-like hyperbranched monomer sample 5.

Example 6

(1) Adding pentaerythritol and acrylonitrile to the reaction kettle in a molar ratio of 1:4.3; under the condition of a solvent-free ice bath, slowly adding a 30% strength NaOH solution to the reaction kettle, keeping at room temperature and stirring with $N_2$ for 8~48 h; after the reaction is completed, water is added, followed by extraction with ethyl acetate; the extract is dried over anhydrous sodium sulfate, and the solvent is distilled off under reduced pressure to obtain the intermediate A.

(2) The intermediate A is added to concentrated hydrochloric acid and refluxed for 5 h to obtain intermediate B.

(3) Adding tris(hydroxymethyl)aminomethane, acrylonitrile, and 1,4-dioxane to the reaction kettle in a molar ratio of 1:3.2:20, the mount of 1,4-dioxane is 10 mL, and slowly adding a 40% strength NaOH solution to the reaction kettle; keeping at room temperature and stirring with $N_2$ for 36 h; after the reaction is completed, the solvent is added, followed by extraction with ethyl acetate; the extract is dried over anhydrous sodium sulfate, and the solvent is distilled off under reduced pressure to obtain an intermediate C.

(4) The intermediate C is added to a saturated HCl methanol solution, and refluxed for 8 h to obtain the intermediate D.

(5) Adding 1-(3-dimethylaminopropyl)-3-ethylcarbodiimide hydrochloride, 1-hydroxybenzotriazole, the intermediate B and the intermediate D to the reaction kettle containing dichloromethane solvent in a molar ratio of 1:1:1:4.2; keeping at room temperature and stirring with $N_2$ for 30 h; after the reaction is completed, it is extracted with dichloromethane, and then washed with saturated brine, dried over anhydrous sodium sulfate, and distilled under reduced pressure to obtain intermediate E.

(6) Adding the intermediate E and butane-diamine in a molar ratio of 1:12 to the reaction kettle containing the solvent, adding butane-diamine at 25~30° C. and stirring the reaction for 48 h; the solvent is then distilled off under reduced pressure to obtain intermediate F.

(7) Under the condition of 25° C., the intermediate F, triethylamine and maleic anhydride are slowly added to the reaction kettle containing the solvent at a molar ratio of 1:12:13, and then raising the temperature to 80° C. and reacting for 24 h; after the reaction is completed, ethyl acetate is added for extraction, and the extract is washed with saturated brine, dried over anhydrous sodium sulfate, and the solvent is distilled off under reduced pressure to obtain the three-dimensional cage-like hyperbranched monomer sample 6.

Figure 2:
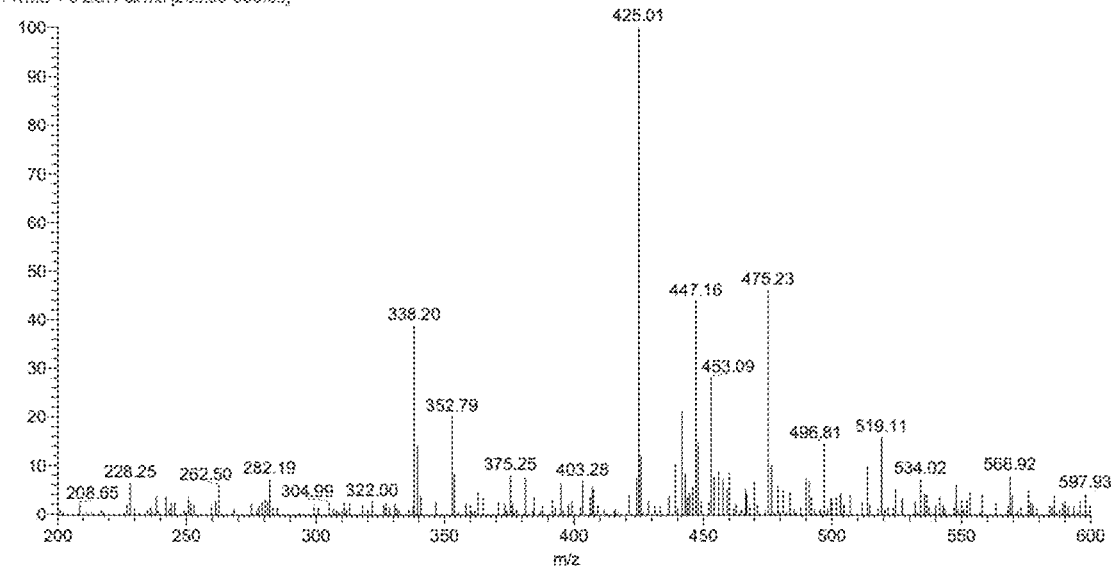
FIG. 2 is a mass spectrum of Intermediate B in Example 1 of the present invention.
Figure 3:
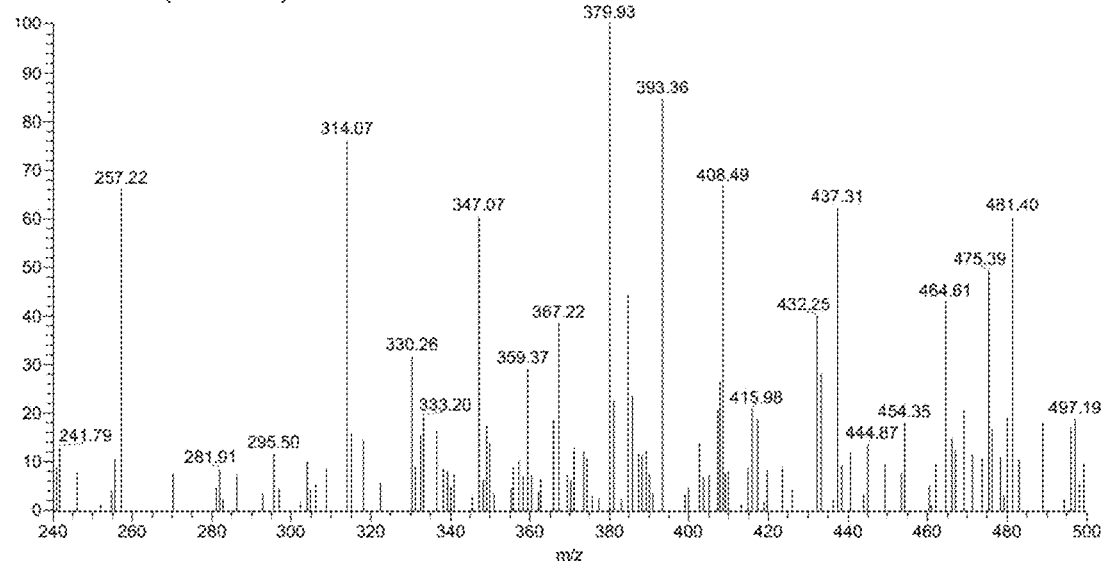
FIG. 3 is a mass spectrum of Intermediate D in Example 1 of the present invention.

The three-dimensional cage-like hyperbranched monomer samples 1 to 6 prepared in Examples 1 to 6 and the corresponding intermediate products were subjected to mass spectrometry testing. In this embodiment, an ion hydrazine mass spectrometer ITMS (ESI, LCQ-fleet) was used for testing. Taking Example 1 as an example, the test results are shown in FIGS. 1 to 4. Among them, FIG. 1 is a mass spectrum of Intermediate A in Example 1 of the present invention; it can be seen from the figure that the measured molecular weight of Intermediate A is 348.90, while the theoretical intermediate A is $C_{17}H_{24}N_4O_4$, and its theoretical molecular weight is 348.40, which is consistent with the measured value; that proves that the substance synthesized in step (1) of the above preparation method is indeed intermediate A. FIG. 2 is a mass spectrum of the intermediate B in Example 1 of the present invention. It can be seen from the figure that the measured molecular weight of the intermediate B is 425.01, while the theoretical intermediate B is $C_{17}H_{28}O_{12}$, and its theoretical molecular weight is 424.40, which is consistent with the measured value; that proves the substance synthesized in step (2) of the above preparation method is indeed intermediate B. FIG. 3 is a mass spectrum of the intermediate D in Example 1 of the present invention. It can be seen from the figure that the measured molecular weight of the intermediate D is 379.93, while the theoretical intermediate D is $C_{16}H_{29}N_{O9}$, and its theoretical molecular weight is 379.41, which is consistent with the measured value; that proves the substance synthesized in step (4) of the above preparation method is indeed intermediate D.

Figure 4:
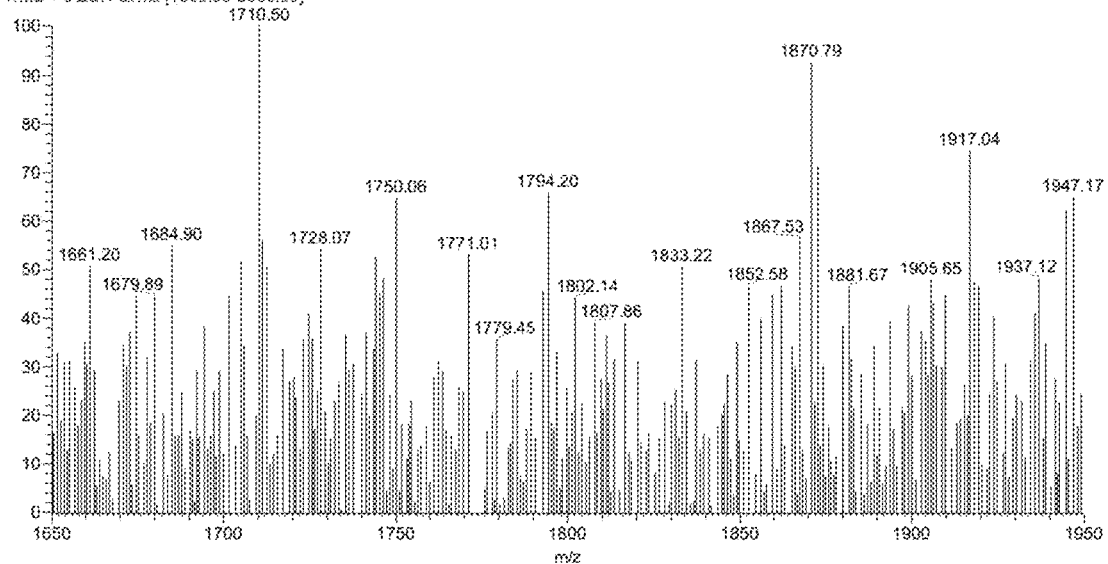
FIG. 4 is a mass spectrum of Intermediate E in Example 1 of the present invention.

FIG. 4 is a mass spectrum of the intermediate E in Example 1 of the present invention. It can be seen from the figure that the measured molecular weight of the intermediate E is 1870.79, while the theoretical intermediate E is $C_{81}H_{136}N_4O_{44}$, and its theoretical molecular weight is 1869.96, which is consistent with the measured value; that proves the substance synthesized in step (5) of the above preparation method is indeed intermediate E. Based on the preparation of intermediate E, through the steps (6) and (7), the branch of the intermediate E is replaced to obtain the aforementioned three-dimensional cage-like hyperbranched monomer. The aforementioned three-dimensional cage-like hyperbranched monomer structure can be prepared through Examples 1 to 6.

In summary, introducing easily polymerizable olefin groups, the carboxyl group and amide group are combined in the three-dimensional cage-like hyperbranched monomer to make the water solubility good, and it can be copolymerized with many other monomers to obtain the three-dimensional cage-like hyperbranched polymer; when used as an additive for wellbore working fluids, due to the hyperbranched structure of the polymer, it has good salt and temperature resistance, and also has viscosity increasing, filtration loss, and flocculation properties; meanwhile, the synthesis method is simple and the cost is low.

It is to be understood, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. The three-dimensional cage-like hyperbranched monomer has the structural formula I:

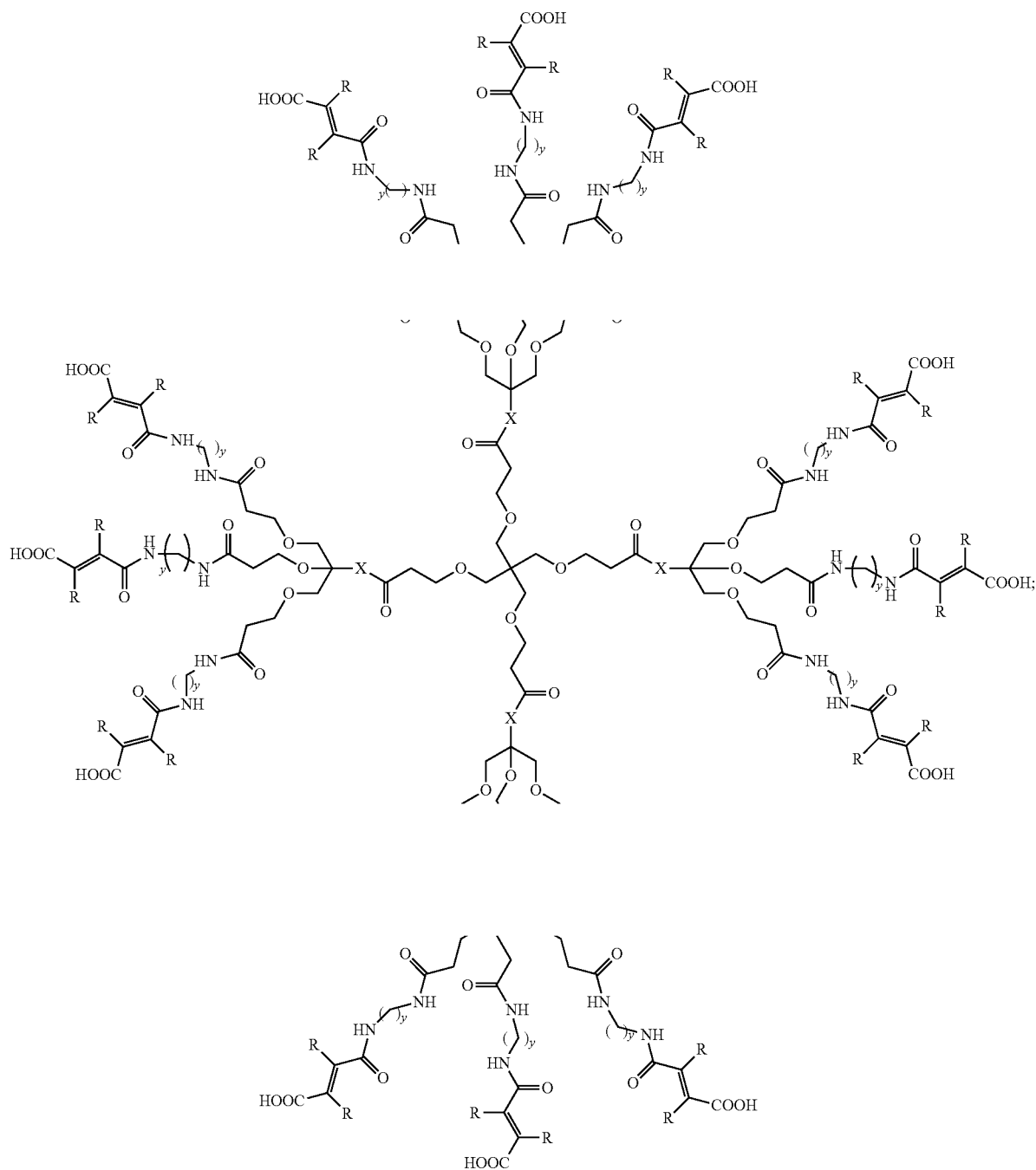

wherein in the structural formula I: X is any one of —O, —S, —NH; y is any integer from 2 to 8; R is —H or —CH₃.

2. The preparation method of the three-dimensional cage-like hyperbranched monomer, including the following steps:
(1) adding pentaerythritol and acrylonitrile to the reaction kettle in a molar ratio of 1:(4~4.5); under the condition of a solvent-free ice bath, slowly adding a 30% strength NaOH solution to the reaction kettle, keeping at room temperature and stirring with N₂ for 8~48 h; after the reaction is completed, a solvent is added, followed by extraction with an extractant; the extract is dried over anhydrous sodium sulfate, and the solvent is distilled off under reduced pressure to obtain an intermediate A, which has the structural formula II:

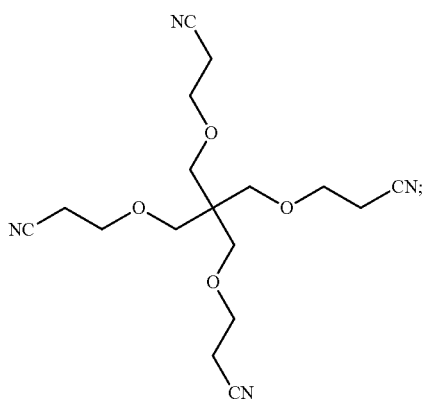

II (2) the intermediate A is added to concentrated hydrochloric acid and refluxed for 3~8 h to obtain intermediate B, whose structural formula is III:

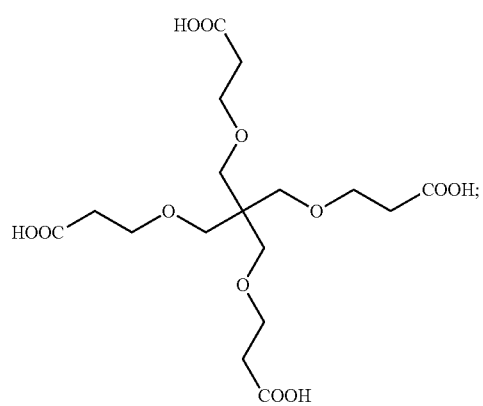

III (3) adding trimethylol-substituted methane, acrylonitrile, and 1,4-dioxane to the reaction kettle in a molar ratio of 1:(3~3.5):20, and slowly adding a 40% strength NaOH solution to the reaction kettle; keeping at room temperature and stirring with $N_2$ for 8~48 h; after the reaction is completed, the solvent is added, followed by extraction with the extractant; the extract is dried over anhydrous sodium sulfate, and the solvent is distilled off under reduced pressure to obtain an intermediate C, which has the structural formula IV:

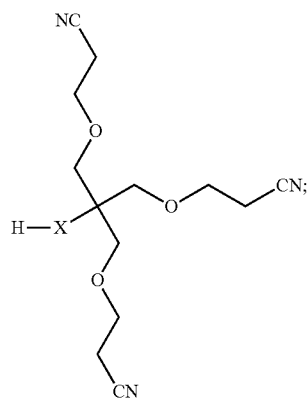

IV

X is any one of —O, —S, —NH;

(4) the intermediate C is added to a saturated HCl methanol solution, and refluxed for 3~8 h to obtain the intermediate D, whose structural formula is V:

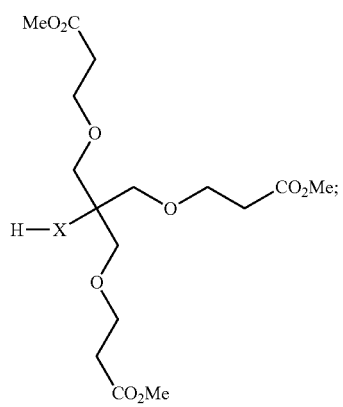

V (5) adding 1-(3-dimethylaminopropyl)-3-ethylcarbodiimide hydrochloride, 1-hydroxybenzotriazole, the intermediate B and the intermediate D to the reaction kettle containing the solvent in a molar ratio of 1:1:1:(4~5); keeping at room temperature and stirring with $N_2$ for 20~48 h; after the reaction is completed, it is extracted with the extractant, and then washed with saturated brine, dried over anhydrous sodium sulfate, and distilled under reduced pressure to obtain intermediate E, which has the structural formula VI:

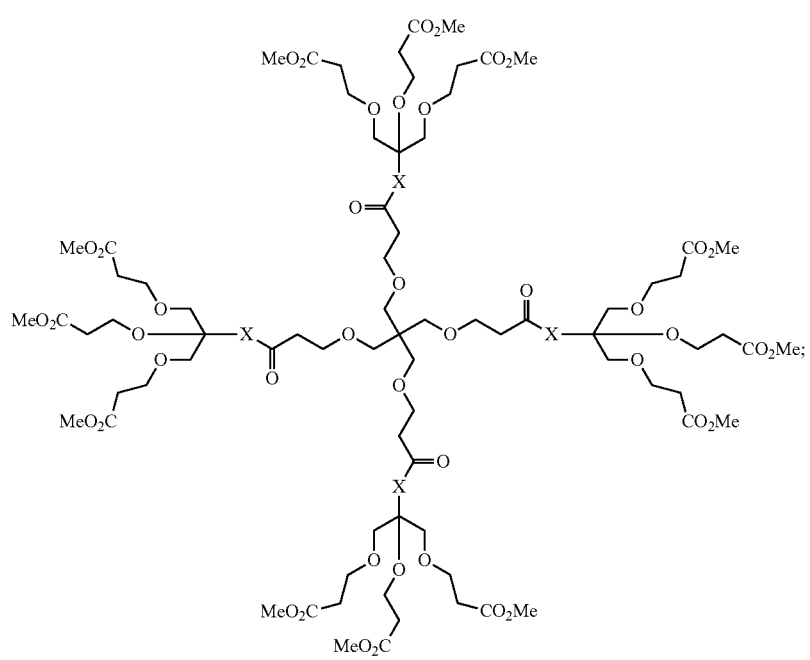

VI

X is any one of —O, —S, —NH;

(6) adding the intermediate E and the diamine in a molar ratio of 1:(12~20) to the reaction kettle containing the solvent, adding the diamine at 25~30° C. and stirring the reaction for 24~48 h; the solvent is then distilled off under reduced pressure to obtain intermediate F, which has the structural formula VII:

y is any integer from 2 to 8;

(7) under the condition of 25° C., the intermediate F, the acid binding agent and the dibasic anhydride are slowly added to the reaction kettle containing the solvent at a molar ratio of 1:12:(12~20), and then raising the temperature to 60~100° C. and reacting for 18~30 h; after the reaction is completed, the extractant is added for

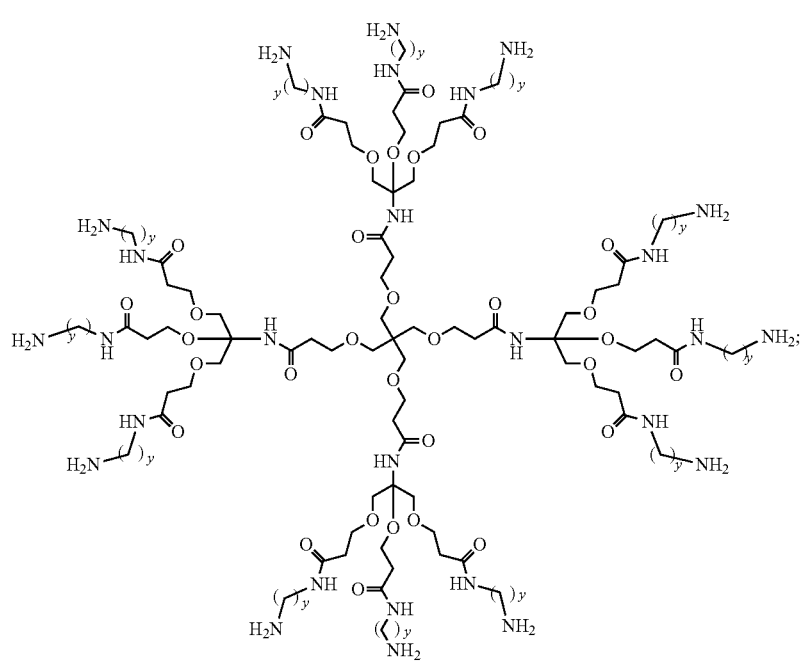

VII extraction, and the extract is washed with saturated brine, dried over anhydrous sodium sulfate, and the solvent is distilled off under reduced pressure to obtain the three-dimensional cage-like hyperbranched monomer according to claim 1.

3. The preparation method of the three-dimensional cage-like hyperbranched monomer according to claim 2, wherein the trimethylol-substituted methane is one of tris(hydroxymethyl)methane, tris(hydroxymethyl)mercaptomethane and tris(hydroxymethyl)aminomethane.

4. The preparation method of the three-dimensional cage-like hyperbranched monomer according to claim 2, wherein the diamine is one of ethylenediamine, propylenediamine, butylenediamine, pentanediamine, hexamethylenediamine, diaminoheptane and octanediamine.

5. The preparation method of the three-dimensional cage-like hyperbranched monomer according to claim 2, wherein the dibasic acid anhydride is maleic anhydride or 2,3-dimethyl maleic anhydride.

6. The preparation method of the three-dimensional cage-like hyperbranched monomer according to claim 2, wherein the solvent is one or a mixture of dioxane, dichloromethane, dichloroethane, chloroform, methanol, water, methanol, ethanol, isopropanol, tert-butanol, diethyl ether, isopropyl ether, petroleum ether, acetone, tetrahydrofuran, N,N-dimethylformamide, N,N-dimethylacetamide, dimethyl sulfoxide and white oil.

7. The preparation method of the three-dimensional cage-like hyperbranched monomer according to claim 2, wherein the acid binding agent is one or a mixture of triethylamine, tri-n-propylamine, tri-n-butylamine, triethylenediamine or N,N,N',N'-tetramethylethylenediamine.

8. The preparation method of the three-dimensional cage-like hyperbranched monomer according to claim 2, wherein the extractant is one or a mixture of ethyl acetate, dichloromethane, chloroform, and dichloroethane.

9. The application of the three-dimensional cage-like hyperbranched monomer according to claim 1, wherein the three-dimensional cage-like hyperbranched monomer is used as an additive for a wellbore working fluid and a polymer emulsion; the wellbore working fluid includes drilling fluid, completion fluid, and fracturing fluid.

\* \* \* \* \*